(12) United States Patent
Levorse, Jr. et al.

(10) Patent No.: US 7,723,277 B2
(45) Date of Patent: May 25, 2010

(54) METHYL CYCLOHEXANE CARBOXYLATES AND THEIR USE IN PERFUME COMPOSITIONS

(75) Inventors: Anthony T. Levorse, Jr., Westfield, NJ (US); Richard A. Weiss, Livingston, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/555,439

(22) Filed: Sep. 8, 2009

(65) Prior Publication Data

US 2009/0326079 A1 Dec. 31, 2009

Related U.S. Application Data

(62) Division of application No. 11/941,159, filed on Nov. 16, 2007, now Pat. No. 7,632,792.

(51) Int. Cl.
*C11D 3/50* (2006.01)
(52) U.S. Cl. .................. 510/106; 512/22; 560/106; 560/133
(58) Field of Classification Search ............ 560/106, 560/113; 510/106; 512/22
See application file for complete search history.

(56) References Cited

U.S. PATENT DOCUMENTS 3,743,719 A * 7/1973 Beroza et al. .................. 424/84

\* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention a method of improving, enhancing or modifying a fragrance formulation through the addition of an olfactory acceptable amount of the following compound:

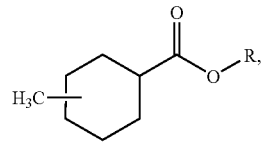

wherein R represents a straight, branched, or cyclic C1 to C5 hydrocarbon moiety containing saturated and/or unsaturated bonds, or a C3 to C5 glycolether, and wherein the methyl substituent is located in the ortho, meta, or para position on the cyclohexane ring.

10 Claims, No Drawings

METHYL CYCLOHEXANE CARBOXYLATES AND THEIR USE IN PERFUME COMPOSITIONS

STATUS OF RELATED APPLICATIONS

This application is a divisional of U.S. Ser. No. 11/941,159, filed Nov. 16, 2007 now U.S. Pat. No. 7,632,792, which is hereby incorporated by reference in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. More specifically, the present invention is directed to the fragrance compounds and a method of improving, enhancing or modifying a fragrance formulation through the addition of an olfactory acceptable amount of methyl cyclohexane carboxylates represented by Formula I set forth below:

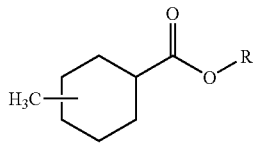

Formula I wherein R represents a straight, branched, or cyclic C1 to C5 hydrocarbon moiety containing saturated and/or unsaturated bonds, or a C3 to C5 glycolether, and wherein the methyl substituent is located in the ortho, meta, or para position on the cyclohexane ring.

Another embodiment of the invention is directed to a method for enhancing a perfume composition by incorporating an olfactory acceptable amount of the methyl cyclohexane carboxylate compounds provided above.

These and other embodiments of the present invention will be apparent by reading the following specification.

DETAILED DESCRIPTION OF THE INVENTION

In Formulae I above, R represents a straight, branched, or cyclic C1 to C5 hydrocarbon moiety containing saturated and/or unsaturated bonds, or a C3 to C5 glycolether, and wherein the methyl substituent is located in the ortho, meta, or para position on the cyclohexane ring. Suitable straight hydrocarbon moieties include methyl, ethyl, propyl, butyl, pentyl, and the like. Suitable branched hydrocarbon moieties include isopropyl, sec-butyl, tert-butyl, iso-butyl, sec-pentyl, tert-pentyl, and the like. Suitable hydrocarbon moieties containing double bonds include ethene, 1-propene, 2-propene, 1-butene, 2-butene, 3-butene, isobutene, 3-methyl-3-butene, and the like. Suitable glycolethers include 2-methoxyethyl, 2-ethoxyethyl, and 2-ethoxyethyl-1-methylethyl.

In another embodiment of the invention, the novel compounds of the invention are represented by the following structures:

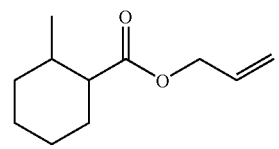

Structure I

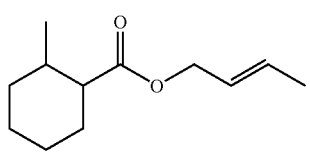

Structure II

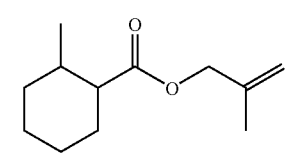

Structure III

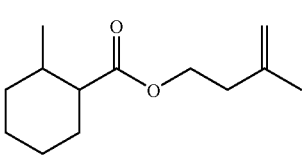

Structure IV

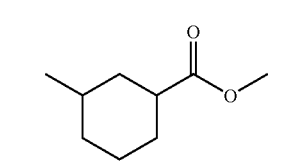

Structure V

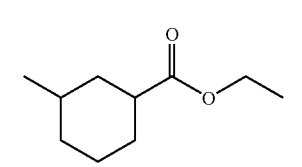

Structure VI

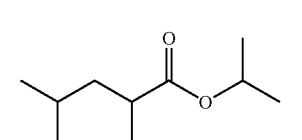

Structure VII

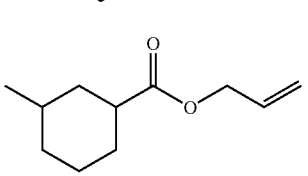

Structure VIII

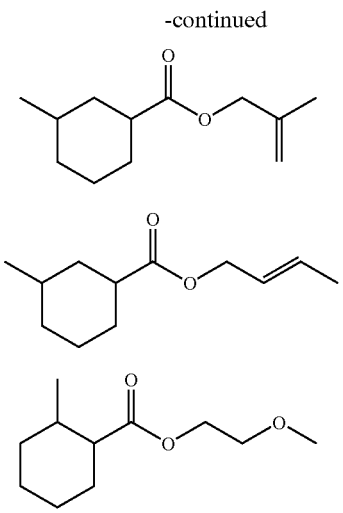

Those with the skill in the art will appreciate that

Structure I is allyl 2-methyl cyclohexane carboxylate;

Structure II is crotyl 2-methyl cyclohexane carboxylate;

Structure III is methallyl 2-methyl cyclohexane carboxylate;

Structure IV is 3-methyl-3-butenyl 2-methyl cyclohexane carboxylate;

Structure V is methyl 3-methyl cyclohexane carboxylate;

Structure VI is ethyl 3-methyl cyclohexane carboxylate;

Structure VII is 1-methylethyl 3-methyl cyclohexane carboxylate;

Structure VIII is allyl 3-methyl cyclohexane carboxylate;

Structure IX is 2-methyl-2-propenyl 3-methyl cyclohexane carboxylate;

Structure X is 2-butenyl 3-methyl cyclohexane carboxylate; and

Structure XI is 2-methoxyethyl 2-methyl cyclohexane carboxylate.

The compounds of the present invention may be prepared from the corresponding compounds via a catalytic hydrogenation or a transesterification reaction.

A catalytic hydrogenation reaction can be depicted by a general scheme as follows:

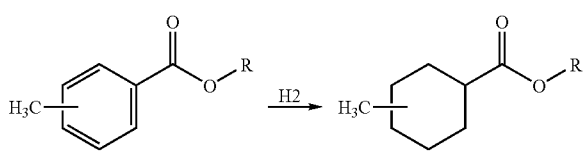

A further transesterification reaction can be carried out if the R group contains an unsaturated bond. A transesterification reaction is depicted by a general scheme as follows:

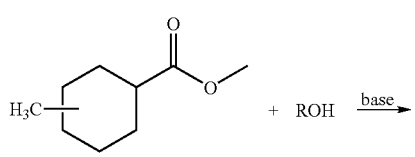

Those with skill in the art will appreciate the reagent ROH is an alcohol, wherein R is defined above.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, Kg is understood to be kilogram, and g be gram. IFF as used in the examples is understood to mean International Flavors & Fragrances Inc., New York, N.Y., USA.

EXAMPLE I

Methyl m-toluate: A 3 L reaction flask was charged with methyl m-toluic acid (0.5 kg), anhydrous methanol (2 L), and sulfuric acid (100 g). The mixture was heated to reflux (65° C.) and aged for 14-20 hours, then cooled to an ambient temperature, and the acid was quenched with a two molar equivalent of sodium acetate. Methanol was distilled out of the flask and the mixture was washed with 1 L brine. The crude product was vacuum distilled to give 480 g of methyl m-toluate, which had a boiling point of 113° C. at a pressure of 25 mmHg.

Other toluates used in the following examples that were used as the starting materials to afford the claimed compounds can also be prepared with corresponding toluic acids using the reaction depicted here above.

EXAMPLE II

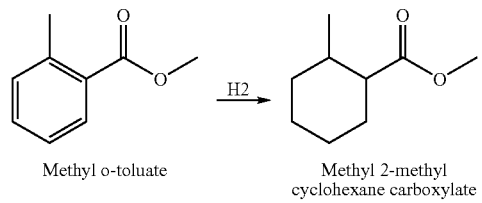

Methyl o-toluate → Methyl 2-methyl cyclohexane carboxylate

Methyl 2-methyl cyclohexane carboxylate: A 2 L zipper autoclave was charged with methyl o-toluate (1 Kg) and ruthenium on alumina (available from Heraeus Holding) (50 g). The mixture was then placed under a hydrogen atmosphere (500 psig). The system was heated to 140-150° C. and aged for 4-6 hours, then cooled to an ambient temperature, and the hydrogen atmosphere was replaced with a nitrogen atmosphere. Ruthenium catalyst was removed by vacuum filtration over celite. The crude product was vacuum distilled to give 950 g of methyl 2-methyl cyclohexane carboxylate, which had a boiling point of 109° C. at a pressure of 49 mmHg.

H1 NMR: 3.6 ppm (s, 3H), 1.95 ppm (t, 1H, J=11.39 Hz, of d, J=3.44 Hz), 1.83-1.87 ppm (m, 1H), 1.66-1.77 ppm (m, 3H), 1.55-1.65 ppm (m, 1H), 1.44 ppm (q, 1H, J=12.63 Hz, of d, J=3.54 Hz), 1.15-1.38 ppm (m, 2H), 0.92-1.04 ppm (m, 1H), 0.87 ppm (d, 3H, J=6.47 Hz).

The compound was described as having fruity and pineapple notes.

EXAMPLE III

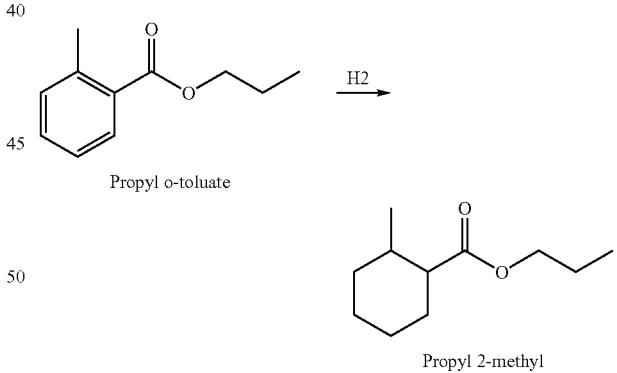

Propyl o-toluate → Propyl 2-methyl cyclohexane carboxylate

Propyl 2-methylcyclohexane carboxylate: 950 g of propyl 2-methylcyclohexane carboxylate was prepared with 1 Kg of propyl o-toluate. The final product had a boiling point of 93° C. at a pressure of 9 mmHg.

H1 NMR: 3.97-4.07 ppm (m, 2H), 2.47-2.53 ppm (m, 1H), 2.15 ppm (br. s, 1H), 1.58-1.76 ppm (m, 6H), 1.47-1.57 ppm (m, 2H), 1.34-1.41 ppm (m, 1H), 1.25-1.32 ppm (m, 1H), 0.90-0.97 ppm (m, 6H).

The compound was described as having fruity and menthol notes.

EXAMPLE IV

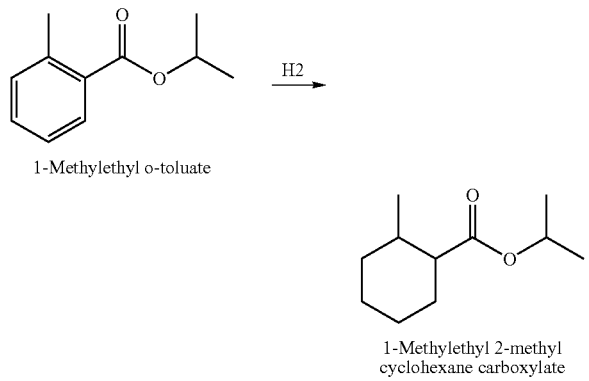

1-Methylethyl o-toluate

1-Methylethyl 2-methyl cyclohexane carboxylate

1-Methylethyl 2-methyl cyclohexane carboxylate: 830 g of 1-methylethyl 2-methyl cyclohexane carboxylate was prepared with 1 Kg of 1-methylethyl o-toluate. The final product had a boiling point of 116° C. at a pressure of 30 mmHg.

H1 NMR: 4.97-5.06 ppm (m, 1H), 2.42-2.47 ppm (m, 1H), 2.15 ppm (br. s, 1H), 1.66-1.76 ppm (m, 2H), 1.56-1.65 ppm (m, 2H), 1.46-1.55 ppm (m, 2H), 1.33-1.45 ppm (m, 1H), 1.20-1.32 ppm (m, 7H), 0.91 ppm (d, 3H, J=7.09 Hz).

The compound was described as having sweet, creamy, and fruity notes.

EXAMPLE V

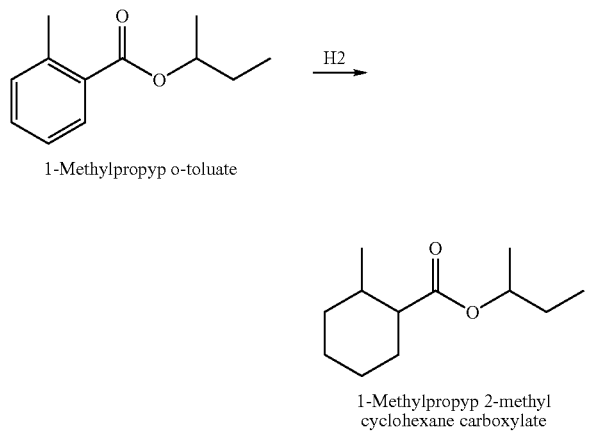

1-Methylpropyp o-toluate

1-Methylpropyp 2-methyl cyclohexane carboxylate

1-Methylpropyp 2-methyl cyclohexane carboxylate: 950 g of 1-methylpropyp 2-methyl cyclohexane carboxylate was prepared with 1 Kg of 1-methylpropyo o-toluate. The final product has a boiling point of 106° C. at a pressure of 12.5 mmHg.

H1 NMR: 4.81-4.87 ppm (m, 1H), 2.44-2.49 ppm (m, 1H), 2.15 ppm (br. s, 1H), 1.45-1.76 ppm (m, 8H), 1.20-1.43 ppm (m, 2H), 1.18-1.20 ppm (m, 3H), 0.87-0.93 ppm (m, 6H).

The compound was described as having fruity and pineapple notes.

EXAMPLE VI

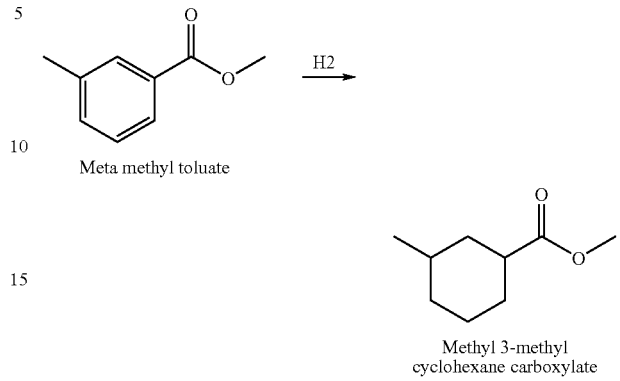

Meta methyl toluate

Methyl 3-methyl cyclohexane carboxylate

Methyl 3-methylcyclohexane carboxylate: 850 g of methyl 3-methylcyclohexane carboxylate was prepared with 1 Kg of meta methyl toluate. The final product has a boiling point of 84° C. at a pressure of 17 mmHg.

H1 NMR: 0.82-0.96 ppm (m, 3H+~59% of 1H), 1.03-1.07 ppm (m, 1H), 1.27-1.91 ppm (m, 7H+~41% of 1H), 2.30 ppm (m, ~59% of 1H), 2.63 ppm (m, ~41% of 1H), 3.64-3.67 ppm (m, 3H)

The compound was described as having fruity and sweet notes.

Example VII

Meta ethyl toluate

Ethyl 3-methyl cyclohexane carboxylate

Ethyl 3-methylcyclohexane carboxylate: 800 g of ethyl 3-methylcyclohexane carboxylate was prepared with 1 Kg of meta ethyl toluate. The final product has a boiling point of 100° C. at a pressure of 31 mmHg.

H1 NMR: 0.84-0.88 ppm (m, 1H), 0.91 ppm (d, ~48% of 3H, J=5.76 Hz), 0.92 ppm (d, ~52% of 3H, J=6.57 Hz), 1.10-1.09 ppm (m, 1H), 1.25 ppm (t, 3H, J=7.13 Hz, of d, J=3.10 Hz), 1.28-1.32 ppm (m, 1H), 1.36-1.73 ppm (m, 3H+~48% of 1H), 1.76-1.84 ppm (m, ~52% of 1H), 1.84-1.97 ppm (m, 2H), 2.25-2.31 ppm (m, ~52% of 1H), 2.61 ppm (pentet, ~48% of 1H, J=5.02 Hz), 4.08-4.16 ppm (m, 2H)

The compound was described as having fruity and sweet notes.

EXAMPLE VIII

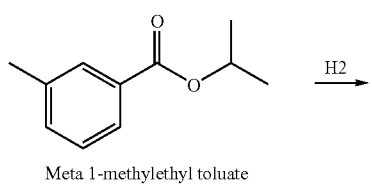

Meta 1-methylethyl toluate

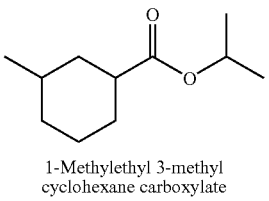

1-Methylethyl 3-methyl
cyclohexane carboxylate

1-Methylethyl 3-methylcyclohexane carboxylate: 950 g of 1-methylethyl 3-methylcyclohexane carboxylate was prepared with 1 Kg of meta 1-methylethyl toluate. The final product has a boiling point of 97° C. at a pressure of 16 mmHg.

H1 NMR: 0.84-0.89 ppm (m, ~54% of 1H), 0.91 ppm (d, ~46% of 3H, J=6.76 Hz), 0.92 ppm (d, ~54% of 3H, J=6.61 Hz), 1.00-1.08 ppm (m, 1H), 1.20-1.31 ppm (m, 1H+~46% of 1H), 1.21 ppm (d, ~54% of 6H, J=6.25 Hz), 1.23 ppm (d, ~46% of 6H, J=6.62 Hz), 1.39-1.92 ppm (m, 6H), 2.21-2.28 ppm (m, ~54% of 1H), 2.56-2.59 ppm (m, ~46% of 1H), 4.96-5.03 ppm (m, 1H)

The compound was described as having fruity and sweet notes.

EXAMPLE IX

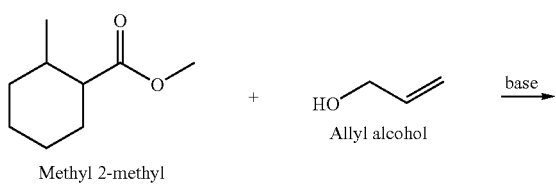

Allyl 2-methyl cyclohexane carboxylate: A reaction flask was charged with methyl 2-methyl cyclohexane carboxylate (500 g), an alcohol (3 equiv.), and solid sodium methoxide (10 g). The reaction mass was heated to 90° C. Methanol and/or a mix of methanol and allyl alcohol was collected in a Dean-Stark apparatus. When no distillate was recovered in the Dean-Stark trap (4-8 hours) the reaction mass was cooled to an ambient temperature, neutralized with acetic acid (12 g), and washed with brine. Purification by vacuum distillation afforded recovered methyl 2-methyl cyclohexane carboxylate and the final product of allyl 2-methyl cyclohexane carboxylate. 365 g of allyl 2-methyl cyclohexane carboxylate was yielded with a boiling point of 96° C. at a pressure of 11 mmHg.

H1 NMR: 5.87-5.97 ppm (m, 1H), 5.32 ppm (d, 1H, J=17.20 Hz, of d, J=1.43 Hz), 5.22 ppm (d, 1H, J=10.43 Hz, of d, J=1.16 Hz), 4.58 ppm (d, 2H, J=5.52 Hz), 1.94-2.01 ppm (t, 1H, J=11.4 Hz, of d, J=3.4 Hz), 1.86-1.91 ppm (m, 1H), 1.62-1.78 ppm (m, 4H), 1.45 ppm (q, 1H, J=12.7 Hz, of d, J=3.4 Hz), 1.18-1.33 ppm (m, 2H), 0.90-1.02 ppm (m, 1H), 0.88 ppm (d, 3H, J=6.46 Hz).

The compound was described as having fruity, herbaceous, and tagette notes.

EXAMPLE X

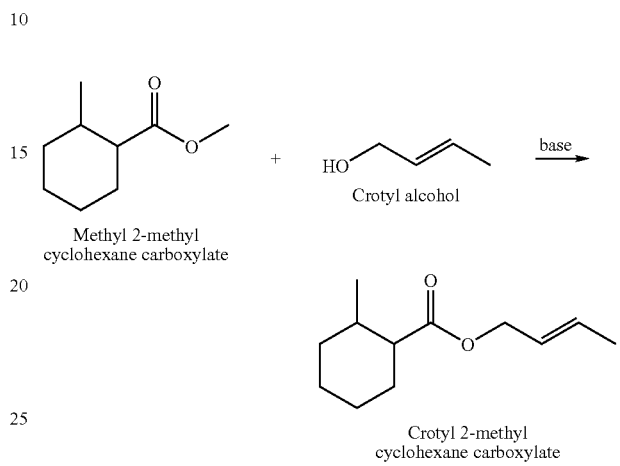

Crotyl 2-methyl cyclohexane carboxylate: 240 g of crotyl 2-methyl cyclohexane carboxylate was prepared using crotyl alcohol. The final product has a boiling point of 115° C. at a pressure of 10 mmHg.

H1 NMR: 5.74-5.83 ppm (m, 1H), 5.54-5.63 ppm (m, 1H), 4.48-4.64 ppm (m, 2H), 2.50 ppm (t, J~75% of 1H, J=9.5 Hz, of d, J=4.4 Hz), 2.15 ppm (br. s, ~75% of 1H), 1.91-1.98 ppm (m, ~25% of 1H), 1.84-1.89 ppm (m, ~25% of 1H), 1.66-1.76 ppm (m, 5H), 1.57-1.66 ppm (m, 2H), 1.49-1.56 ppm (m, 2H), 1.17-1.48 ppm (m, 2H), 0.91 ppm (d, ~75% of 3H, J=7.09 Hz), 0.87 ppm (d, ~25% of 3H, J=6.45 Hz).

The compound was described as having fruity, pineapple, and berry notes.

EXAMPLE XI

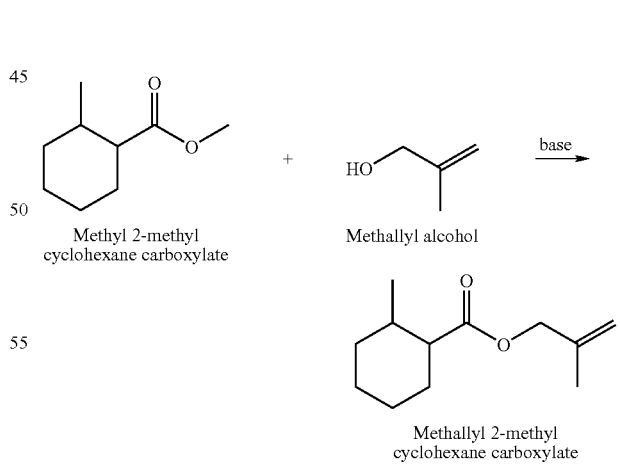

Methallyl 2-methyl cyclohexane carboxylate: 445 g of methallyl 2-methyl cyclohexane carboxylate was prepared using methallyl alcohol. The final product has a boiling point of 113° C. at a pressure of 7 mmHg.

H1 NMR: 4.78 ppm (s, 1H), 4.74 ppm (s, 1H), 4.19 ppm (t, 2H, J=6.81 Hz), 2.34 ppm (t, 2H, J=6.77 Hz), 1.90-1.96 ppm (t, 1H, J=11.36 Hz, of d, J=3.32 Hz), 1.82-1.87 ppm (m, 1H), 1.76 ppm (s, 3H), 1.66-1.77 ppm (m, 3H), 1.59-1.65 ppm (m, 1H), 1.43 ppm (q, 1H, J=12.56 Hz, of d, J=3.44 Hz), 1.17-1.32 ppm (m, 2H), 0.89-1.00 ppm (m, 1H), 0.87 ppm (d, 3H, J=6.42 Hz).

The compound was described as having citrus note.

EXAMPLE XII

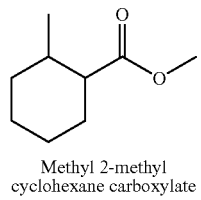

Methyl 2-methyl cyclohexane carboxylate

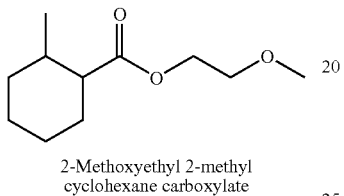

2-Methoxyethyl 2-methyl cyclohexane carboxylate

2-Methoxyethyl 2-methyl cyclohexane carboxylate: 450 g of 2-methoxyethyl 2-methyl cyclohexane carboxylate was prepared using 2-methoxy ethanol. The final product has a boiling point of 78° C. at a pressure of 2 mmHg.

H1 NMR: 4.19-4.25 ppm (m, 2H), 3.58 ppm (t, 2H, J=4.78 Hz), 3.38 ppm (s, 3H), 2.56 ppm (t, 1H, J=9.43 Hz, of d, J=4.49 Hz), 2.17 ppm (br. s, 1H), 1.19-1.76 ppm (m, 8H), 0.92 ppm (d, 3H, J=3.09 Hz).

The compound was described as having low key fruity note.

EXAMPLE XIII

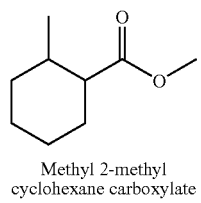

Methyl 2-methyl cyclohexane carboxylate

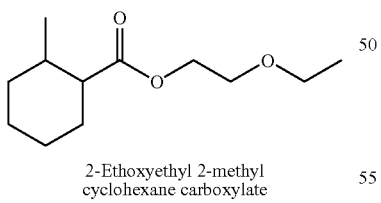

2-Ethoxyethyl 2-methyl cyclohexane carboxylate

2-Ethoxyethyl 2-methyl cyclohexane carboxylate: 475 g of 2-ethoxyethyl 2-methyl cyclohexane carboxylate was prepared using 2-ethoxy ethanol. The final product has a boiling point of 86° C. at a pressure of 2 mmHg.

H1 NMR: 4.18-4.26 ppm (m, 2H), 3.62 ppm (q, 2H, J=4.88 Hz), 3.53 ppm (q, 2H, J=6.99 Hz), 2.53-2.57 ppm (m, 1H), 2.16 ppm (m, 1H), 1.24-1.77 ppm (m, 8H), 1.20 ppm (t, 3H, J=6.99 Hz), 0.92 ppm (d, 3H, J=7.08 Hz).

The compound was described as having low key floral note.

EXAMPLE XIV

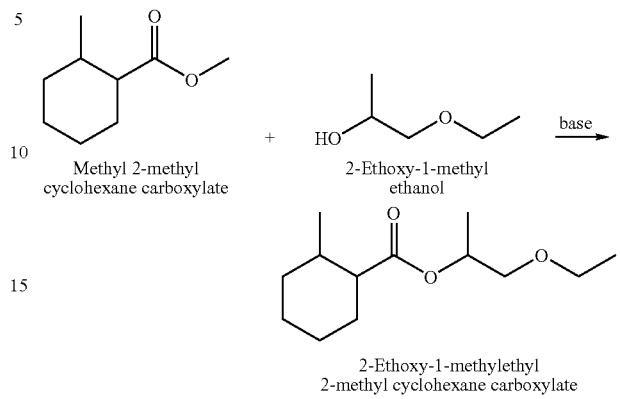

2-Ethoxy-1-methylethyl 2-methyl cyclohexane carboxylate

2-Ethoxy-1-methylethyl 2-methyl cyclohexane carboxylate: 475 g of 2-ethoxy-1-methylethyl 2-methyl cyclohexane carboxylate was prepared using 2-ethoxy-1-methyl ethanol. The final product has a boiling point of 103° C. at a pressure of 3 mmHg.

H1 NMR: 5.06-5.12 ppm (m, 1H), 3.39-3.57 ppm (m, 4H), 2.48-2.53 ppm (m, 1H), 2.15 ppm (br. s, 1H), 1.37-1.73 ppm (m, 8H), 1.16-1.29 ppm (m, 6H), 0.88-0.94 ppm (m, 3H).

The compound was described as having low key sweet note.

EXAMPLE XV

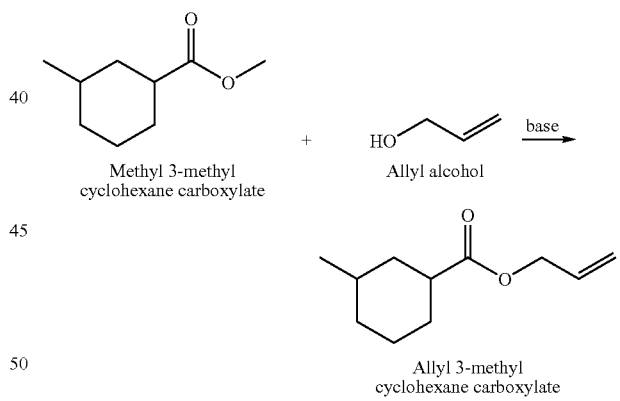

Allyl 3-methyl cyclohexane carboxylate

Allyl 3-methylcyclohexane carboxylate: 518 g of allyl 3-methylcyclohexane carboxylate was prepared using methyl 3-methylcyclohexane carboxylate. The final product has a boiling point of 115° C. at a pressure of 21 mmHg.

H1 NMR: 0.83-0.88 ppm (m, 1H), 0.91 ppm (d, ~22% of 3H, J=6.78 Hz), 0.92 ppm (d, ~78% of 3H, J=6.55 Hz), 1.03-1.11 ppm (m, 1H), 1.26-1.44 ppm (m, 2H), 1.54-1.59 ppm (m, 1H), 1.62-1.69 ppm (m, 1H), 1.77-1.81 ppm (m, 1H), 1.90-1.97 ppm (m, 2H), 2.30-2.36 ppm (m, ~78% of 1H), 2.66 ppm (m, ~22% of 1H), 4.55-4.59 ppm (m, 2H), 5.29 ppm (d, 1H, J=1.56 Hz), 5.32 ppm (d, 1H, J=1.54 Hz), 5.87-5.96 ppm (m, 1H)

The compound was described as having fruity and pineapple notes.

EXAMPLE XVI

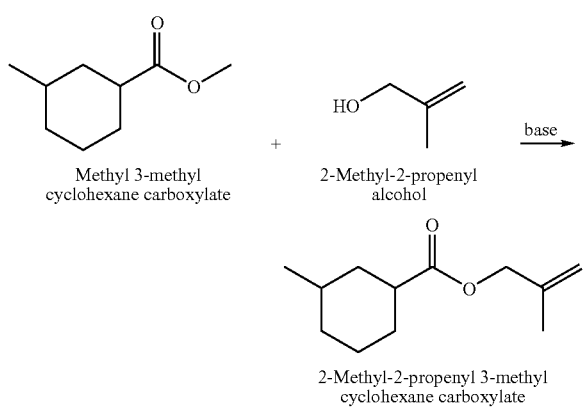

2-Methyl-2-propenyl 3-methylcyclohexane carboxylate: 570 g of 2-methyl-2-propenyl 3-methylcyclohexane carboxylate was prepared with a boiling point of 114° C. at a pressure of 14 mmHg.

H1 NMR: 0.83-0.92 ppm (m, ~78% of 1H), 0.92 ppm (d, 3H, J=6.44 Hz), 1.04-1.12 ppm (m, 1H), 1.25-1.81 ppm (m, 5H+~22% of 1H), 1.75 ppm (s, 3H), 1.90-2.00 ppm (m, 2H), 2.31-2.39 ppm (m, ~78% of 1H), 2.68 ppm (t, ~22% of 1H, J=4.96 Hz), 4.48-4.51 ppm (2s, 2H), 4.91 ppm (s, 1H), 4.96 ppm (s, 1H)

The compound was described as having fruity and pineapple notes.

EXAMPLE XVII

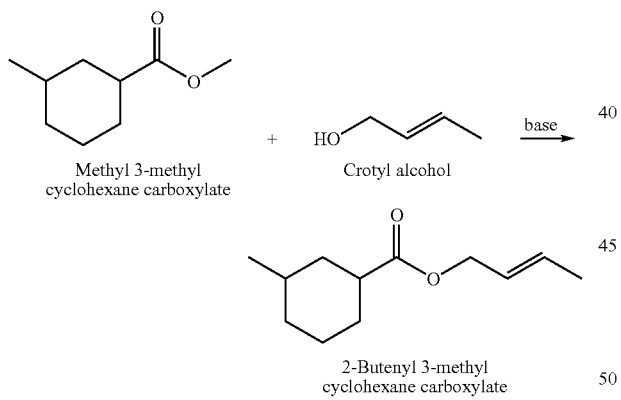

2-Butenyl 3-methylcyclohexane carboxylate: 350 g of 2-butenyl 3-methylcyclohexane carboxylate was prepared using crotyl alcohol. The final product has a boiling point of 120° C. at a pressure of 16 mmHg.

H1 NMR: 0.83-0.93 ppm (m, ~46% of 1H), 0.89-0.92 ppm (d, 3H, J=6.67 Hz), 1.01-1.10 ppm (m, 1H), 1.25-1.32 ppm (m, 1H+~54% of 1H), 1.34-1.50 ppm (m, 1H), 1.51-1.71 ppm (m, 2H), 1.71-1.73 ppm (d, 3H, J=6.50 Hz+~46% of 1H), 1.75-1.81 ppm (m, ~54% of 1H), 1.84-1.97 ppm (m, 2H), 2.27-2.33 ppm (m, ~54% of 1H), 2.63 ppm (t, ~46% of 1H, J=4.84 Hz), 4.48-4.51 ppm (m, 2H), 5.54-5.62 ppm (m, 1H), 5.74-5.82 ppm (m, 1H)

The compound was described as having fruity and pineapple notes.

EXAMPLE XVIII

The fragrance formulas exemplified as follows demonstrate that methyl cyclohexane carboxylates impart a fruity/floral character.

Fruity/Floral Musk Fragrance:

| Fragrance Ingredient | Parts by wt |
|---|---|
| Allyl Caproate | 10 |
| Leaf Alcohol | 5 |
| Kharismal ® | 15 |
| Seveniff ® | 100 |
| Alpha Damascone | 5 |
| Cashmeran ® | 10 |
| Nebulone ® | 50 |
| Iso E Super ® | 100 |
| Phenoxanol ® | 65 |
| Vivaldie ® | 20 |
| Verdox ® | 70 |
| Undecavertol | 5 |
| Ylanganate ® | 45 |
| Applelide ® | 40 |
| Methyl 3-methyl cyclohexane carboxylate | 45 |
| Total | 540 |

Fruity/Floral Accord for Female Perfume:

| Fragrance Ingredient | Parts by Wt |
|---|---|
| Salicynalva ® | 80 |
| Delta Damascone | 25 |
| Gamma Decalactone | 2 |
| Dimethyloctenol | 10 |
| Phenyl ethyl alcohol | 20 |
| Montaverdi ® | 5 |
| Geraniol | 150 |
| Linalool | 50 |
| Iso E Super ® | 123 |
| Cashmeran ® | 25 |
| Applelide ® | 100 |
| Galbascone ® | 15 |
| Leaf Alcohol | 5 |
| Globanone ® | 20 |
| Aldehyde C10 | 30 |
| Kharismal ® | 25 |
| Vanillin | 5 |
| Methyl 3-methyl cyclohexane carboxylate | 10 |
| Total | 700 |

What is claimed is:

1. A method of improving, enhancing or modifying a fragrance formulation through the addition of an olfactory acceptable amount of a compound:

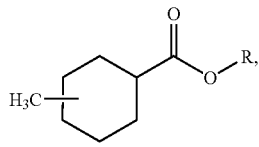

wherein R is selected from the group consisting of $CH_2CH=CH_2$, $CH_2CH=CHCH_3$, $CH_2C(CH_3)=CH_2$, and $CH_2CH_2C(CH_3)CH_2$, and wherein the methyl substituent is located in the ortho position on the cyclohexane ring.

2. The method of claim 1, wherein the compound is:

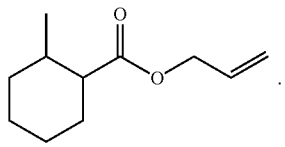

3. The method of claim 1, wherein the compound is:

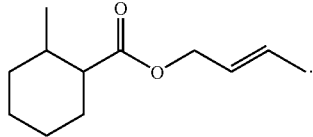

4. The method of claim 1, wherein the compound is:

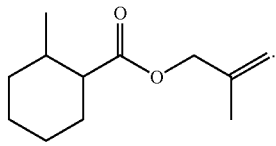

5. The method of claim 1, wherein the compound is:

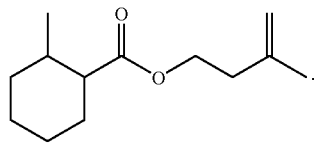

6. The method of claim 1, wherein the fragrance formulation is incorporated into a product selected from the group consisting of a perfume, a cologne, a toilet water, a cosmetic product, a personal care product, a fabric care product, a cleaning product, and an air freshener.

7. The method of claim 6, wherein the cleaning product is selected from the group consisting of a detergent, a dishwashing composition, a scrubbing compound, and a window cleaner.

8. The method of claim 1, wherein the amount is from about 0.005 to about 10 weight percent of the fragrance formulation.

9. The method of claim 1, wherein the amount is from about 0.5 to about 8 weight percent of the fragrance formulation.

10. The method of claim 1, wherein the amount is from about 1 to about 7 weight percent of the fragrance formulation.

* * * * *